United States Patent [19]

Stepto et al.

[11] Patent Number: 5,405,564
[45] Date of Patent: Apr. 11, 1995

[54] METHOD OF FORMING SHAPED ARTICLES MADE FROM PRE-PROCESSED STARCH

[75] Inventors: Robert F. T. Stepto, Riehen; Ivan Tomka, Lenzburg; Markus Thoma, Riehen, all of Switzerland

[73] Assignee: Warner-Lambert Company, Morris Plains, N.J.

[21] Appl. No.: 122,256

[22] Filed: Sep. 15, 1993

Related U.S. Application Data

[63] Continuation of Ser. No. 620,230, Nov. 29, 1990, abandoned, which is a continuation of Ser. No. 209,402, Jun. 20, 1988, abandoned.

[30] Foreign Application Priority Data

Aug. 18, 1987 [GB] United Kingdom ............... 8719485

[51] Int. Cl.$^6$ .................... B29C 45/00; B29C 47/00
[52] U.S. Cl. ...................... 264/115; 264/211.11; 264/328.1; 264/328.18; 264/330
[58] Field of Search ........... 264/328.1, 328.4, 328.16, 264/328.18, 115, 211.11, 330

[56] References Cited

U.S. PATENT DOCUMENTS

| | | | |
|---|---|---|---|
| 2,412,213 | 12/1946 | Groen | 260/234 |
| 3,038,895 | 6/1962 | Rutenberg et al. | 260/233.3 |
| 3,074,803 | 1/1963 | McGowan et al. | 106/38.5 |
| 3,117,014 | 1/1964 | Klug | 106/213 |
| 3,184,335 | 5/1965 | Germino et al. | 127/71 |
| 4,061,610 | 12/1977 | Glowaky et al. | 260/17.4 ST |
| 4,076,846 | 2/1978 | Nakatsuka et al. | 426/62 |
| 4,125,495 | 11/1978 | Griffin | 260/17.4 ST |
| 4,218,350 | 8/1980 | Griffin | 260/17.4 ST |
| 4,232,047 | 11/1980 | Sair et al. | 426/96 |
| 4,673,438 | 6/1987 | Wittwer et al. | 106/126 |
| 4,738,724 | 4/1988 | Wittwer et al. | 106/213 |
| 4,900,361 | 2/1990 | Sachetto et al. | 106/213 |

FOREIGN PATENT DOCUMENTS

| | | | |
|---|---|---|---|
| 0118240 | 9/1984 | European Pat. Off. | C08L 3/00 |
| 1592062 | 7/1981 | United Kingdom | C08L 101/00 |
| 2190093 | 11/1987 | United Kingdom | C08L 3/00 |

*Primary Examiner*—Allan R. Kuhns
*Attorney, Agent, or Firm*—Fitzpatrick, Cella, Harper & Scinto

[57] ABSTRACT

The invention refers to a process of forming shaped articles from starch, which process comprises:
  (a) heating a composition comprising a pre-processed and essentially destructurized starch/water material, at a water content in the range of from 10 to 20% by weight based on the weight of the composition to a temperature sufficient to essentially destructure the starch.
  (b) transferring the melt to a mold while maintaining said water content and
  (c) cooling the melt in the mold to a temperature below its glass transition temperature to form a solid shaped article and articles made by this process.

23 Claims, 7 Drawing Sheets

METHOD OF FORMING SHAPED ARTICLES MADE FROM PRE-PROCESSED STARCH

This application is a continuation of application Ser. No. 07/620,230, filed Nov. 29, 1990, now abandoned, which in turn is a continuation of application Ser. No. 07/209,402, filed Jun. 20, 1988, now abandoned.

The present invention is directed to shaped articles made from pre-processed starch.

It is known that natural starch which is found in vegetable products and which contains a defined amount of water, can be treated at an elevated temperature and in a closed vessel, thereby at elevated pressure, to form a melt. The process is conveniently carried out in an injection molding machine or extruder. The starch is fed through the hopper onto a rotating, reciprocating screw. The feed material moves along the screw towards the tip. During this process, its temperature is increased by means of external heaters around the outside of the barrel and by the shearing action of the screw. Starting in the feed zone and continuing in the compression zone, the particulate feed becomes gradually molten. It is then conveyed through the metering zone, where homogenization of the melt occurs, to the end of the screw. The molten material at the tip can then be further treated by injection molding or extrusion or any other known technique to treat thermoplastic melts, to obtain shaped articles.

This treatment, which is described in the European Patent Application No. 84 300 940.8 (Publication No. 118 240) yields an essentially destructurized starch. The reason for this being that the starch is heated above the melting and glass transition temperatures of its components so that they undergo endothermic transitions. As a consequence a melting and disordering of the molecular structure of the starch granules takes place, so that an essentially destructurized starch is obtained. The expression "pre-processed starch" defines such essentially destructurized starch obtained by such thermoplastic melt formation.

Although articles obtained by injection molding of natural starch are useful, it has been found, that the shaped articles obtained therefrom show a relatively low physical strength. It has further been found that the process itself shows a relatively high instability due to the high dependency of the melt viscosity on the shear rate within the screw barrel which renders the processing for example by injection molding or extrusion more sensitive to conditions of screw speed, temperature, pressure and/or water content and reduces the average quality of the obtained articles.

In this process of injection molding starch, there are two important steps, namely (A) the destructurizing step, i.e. to heat the starch granules above the melting points and the glass transition temperatures of their components to effect the high temperature transitions of the molecular structure and (B) the molding step, i.e. to form the shaped article e.g. by injection molding.

It has now been surprisingly found that the described difficulties are overcome if the mentioned two steps are separated from each other, i.e. the destructurized starch obtained in step (A) is solidified before heating it up again in a screw barrel to finally produce the shaped article. It has been found that by separating the destructurizing step (A) from the molding step (B) a shaped article with considerably improved physical properties is obtained and the molten material in the screw barrel, when carrying out step (B) shows a much reduced dependency of viscosity on the shear rate which again reflects itself in improved flow characteristics and an improved average quality of the produced shaped articles.

The present invention refers to a process of forming shaped articles from starch, which process comprises:
(a) heating a composition comprising a pre-processed, and essentially destructurized starch/water material, at a water content in the range of from 10 to 20% by weight based on the weight of the composition to a temperature sufficient to essentially destructure the starch to form a melt;
(b) transferring the melt to a mold while maintaining said water content and
(c) cooling the melt in the mold to a temperature below its glass transition temperature to form a solid shaped article.

The invention further refers to shaped articles obtained by this process.

Such a pre-processed starch/water material is obtained by thermoplastic melt formation of starch as described supra.

DETAILED DESCRIPTION OF THE INVENTION

Figure 1:
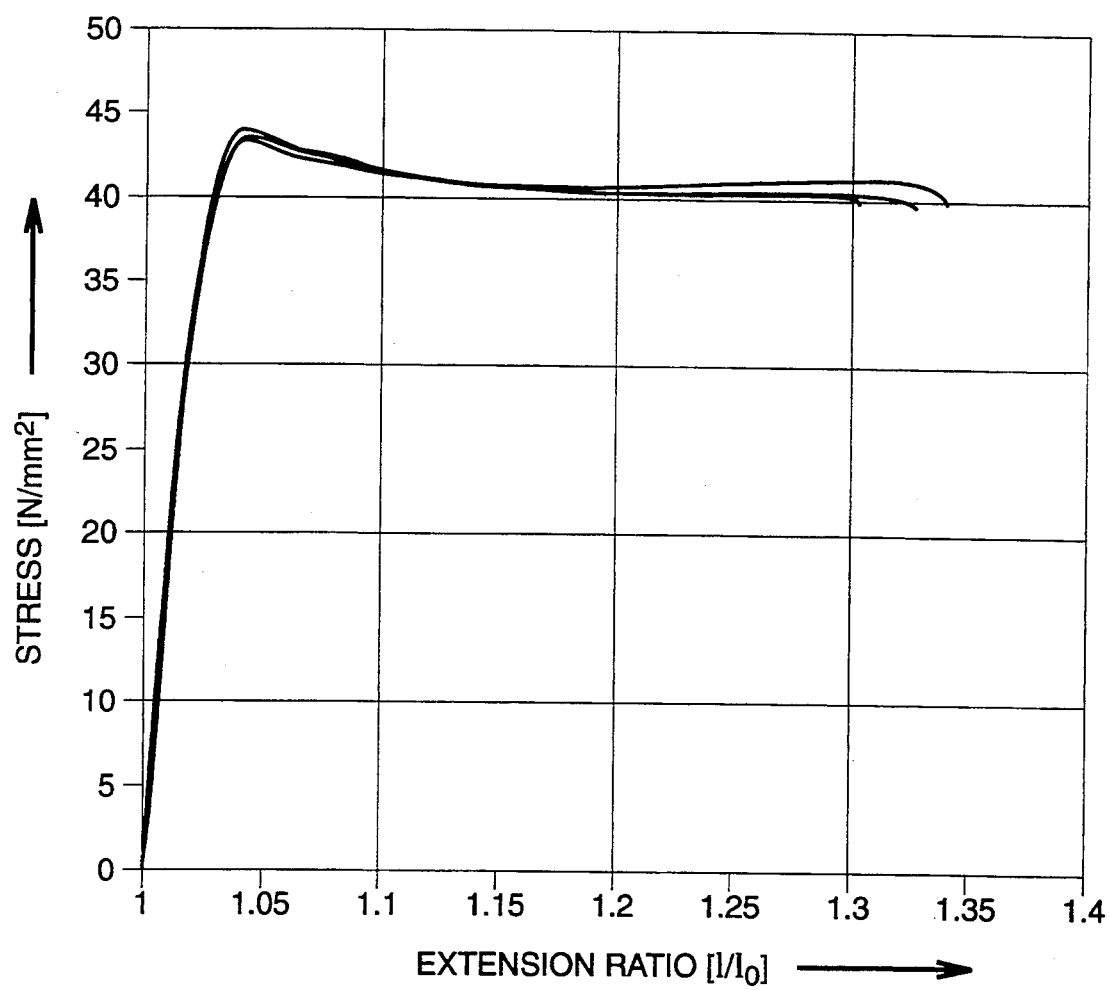
FIG. 1 illustrates the stress/strain behavior of starch processed at a residence time of 450 seconds and a screw speed of 75 rpm.

It is-interesting to note that the improvements obtained as so described are not a function of prolonged residence time of the starch within the screw barrel. The same residence time of the starch material in the molten state in the screw barrel will result in improved product quality if the steps (A) and (B) are carried out separately.

The term "starch" is to be understood as chemically essentially non-modified starch. As such it includes for example carbohydrates of natural, vegetable origin, composed mainly of amylose and/or amylopectin. It may be extracted from various plants, such as potatoes, rice, tapioca, corn, and cereals such as rye, oats and wheat. Preferred is potato starch and corn starch, especially potato starch. It further includes physically modified starch, such as gelatinized or cooked starch, starch with a modified acid value (pH), e.g. where acid has been added to lower its acid value to a range of about 3 to 6. Further is included starch, e.g. potato starch, in which the types and concentrations of the cations associated with the phosphate groups of the starch have been modified to influence processing conditions e.g. temperature and pressure.

Such starch is suitably heated for destructurization in a screw barrel of an extruder above the melting points and the glass transitions point of its components for a time long enough to effect destructurization, which is generally between 3 and 10 minutes, depending on the process parameters. The temperature is preferably within the range of about 120° C. to 190° C., preferably within the range of 130° C. to 190° C. depending on the type of starch used. For this destructurization, the starch material is heated preferably in a closed volume. A closed volume can be a closed vessel or the volume created by the sealing action of the unmolten feed material as happens in the screw of injection molding or extrusion equipment. In this sense the screw barrel of an injection molding machine or an extruder is to be understood as being a closed vessel. Pressures created in a closed volume correspond to the vapour pressure of water at the used temperature but of course pressure may be applied and/or generated as normally occurs in a screw barrel. The preferred applied and/or generated pressures are in the range of the pressures which occur in extrusion or injection molding processes and known per se, i.e. from zero to $150 \times 10^5$ N/m$^2$, preferably from zero to $100 \times 10^5$ N/m$^2$ and most preferably from zero to $80 \times 10^5$ N/m$^2$.

The melt of destructurized starch so obtained is extruded first (step A), cooled to solidify and cut into granules before it is further used in injection molding or pressure molding techniques (step B).

The water content of the pre-processed and essentially destructurized starch/water material used according to the present invention (for step B) has a water content in the range of about 10 to 20% by weight of the composition, preferably 12% to 19% and more preferably 14% to 18% by weight, calculated to the weight of the composition.

This destructurized starch/water material according to this invention is heated essentially above the melting points and glass transition temperatures of its components (step B). Such temperature is generally within the range of about 80° to 200° C., preferably within the range of about 120° to 190° C. and with the range of about 140° to 180° C. These temperatures will essentially destructure the starch to form a melt, i.e. a thermoplastic melt.

The minimum pressure (in step B) corresponds to the water vapour pressure produced at these temperatures. The process is carried out in a closed volume i.e. in the range of pressures which occur in extrusion and injection molding processes such as from zero to $150 \times 10^5$ N/m$^2$ preferably from zero to $100 \times 10^5$ N/m$^2$ and most preferably from zero to $80 \times 10^5$ N/m$^2$.

When forming a shaped article by extrusion, the pressures are preferably as mentioned above. If the melt of the destructurized starch composition according to this invention is injection molded, the range of pressures used is from $300 \times 10^5$ N/m$^2$ to $3000 \times 10^5$ N/m$^2$, preferably $700 \times 10^5$ to $2200 \; 10^5$ N/m$^2$.

The starch material of the present invention may contain or may be mixed with additives, such as extenders, lubricants, plasticizers and/or coloring agents;

These additives may be added before the destructurizing step (step A) or after this step i.e., mixed with the solid granules of the destructurized starch, depending on the intended use of the destructurized starch.

The extenders suitable for use herein include gelatin, vegetable proteins such as sunflower protein, soybean proteins, cotton seed proteins, peanut proteins, rape seed proteins, blood proteins, egg proteins, acrylated proteins, water-soluble polysaccharides; such as alginates, carrageenans, guar gum, agar-agar, gum arabic and related gums (gum ghatti, gum karaya, gum tragacauth) pectin, water-soluble derivatives of cellulose, such as alkylcelluloses hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxpropylmethylcellulose, hydroxybutylmethylcellulose, cellulose esters and hydroxycellulose esters such as cellulose acetylphthalate (CAP), hydroxypropylmethcellulose (HPMCP); carboxyalkylcelluloses, carboxyalkylcelluloses, carboxyalkylcellulose esters such as carboxymethylcellulose and their alkali metal salts, water-soluble synthetic polymers, such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone, polycrotonic acids, and phtnulated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired, and other similar polymers.

Such extenders may be added in any desired amount, preferably up to and including 50%, more preferably within the range of 3% to 10% based on the weight of all components.

Further additives include inorganic fillers, such as the oxides of magnesium, aluminum, silicon, titanium, preferably in a concentration in the range of about 0.02 to 3% by weight, more preferably about 0.02 to 1% based on the weight of all components.

Further examples of additives are plasticizers which include polyalkylene oxides, such as polyethylene glycols, polypropylene glycols, polyethylene-propylene glycols; organic plasticizers with low molecular weights, such as glycerol, glycerol monoacetate, diacetate or triacetate; propylene glycol, sorbitol, sodium diethylsulfosuccinate, triethyl citrate, tributyl citrate, added in the range of from about 0.5 to 15%, preferably ranging from about 0.5 to 5% based on the weight of all the components.

Examples of coloring agents include known azo dyes, organic or inorganic pigments, or coloring agents of natural origin. Inorganic pigments are preferred, such as the oxides of iron or titanium, these oxides, known per se, being added in concentrations ranging from 0.001 to 10%, preferably 0.5 to 3%, based on the weight of all the components.

The sum of the plasticizer and water contents should preferably not exceed 25%, and should most preferably not exceed 20%, based on the weight of all the components.

Additional compounds may further be added to improve the flow properties of the starch material such as animal or vegetable fats, preferably in their hydrogenated form, especially those which are solid at room temperature. These fats have a melting point of 50° C. or higher. Preferred are triglycerides with $C_{12}$-, $C_{14}$-, $C_{16}$-, and $C_{18}$-fatty acids.

These fats may be added without extenders or plasticizers.

Alternatively, these fats may advantageously be added together with mono- and/or diglycerides or phosphatides, especially lecithin. The mono- and diglycerides are preferably derived from the types of fats described above, i.e. with $C_{12}$-, $C_{14}$-, $C_{16}$-, and $C_{18}$-fatty acids.

The total amounts used of the fats, mono-, diglycerides and/or lecithins are up to 5%, and preferably within the range of about 0.5 to 2% by weight of the total composition.

It is further recommended to add silicon dioxide or titanium dioxide in a concentration of about 0.02 to 1% by weight of the total composition. These compounds act as texturizing agents.

The materials described herein on heating and in a closed vessel, (i.e., under controlled water-content and pressure conditions) form a melt with thermoplastic properties. Such a melt may be used in various techniques just like thermoplastic materials. These techniques include injection molding, blow molding, extrusion and coextrusion (rod, pipe and film extrusion), compression molding, to produce known articles as produced with these techniques. These articles include bottles, sheets, films, packaging materials, pipes, rods, laminates, sacks, bags and pharmaceutical capsules.

The following examples further explain the invention.

EXAMPLE 1

(a) Preparation of starch granules.

Natural potato starch, a lubricant/release agent (hydrogenated fat) and a melt flow accelerator (lecithin), are mixed together in the relative proportions in a powder mixer for 10 minutes so that a composition consisting of 81,3 parts of natural potato starch, one part of the hydrogenated triglyceride containing the fatty acids $C_{18}$: $C_{16}$: $C_{14}$ in a ratio of 65:31:4 weight percent, 0.7 parts lecithin, and 17 parts water in the form of a freely flowing powder is obtained. This material was then fed to the hopper of an extruder. In the screw barrel the powder was melted. The temperature within the barrel was measured to be 165° C., the average total residence time was 12 minutes (approx. 10 minutes heating time, approx. 2 minutes in molten state) and the pressure generated was equal to the vapour pressure of the moisture present in the volume of the extruder barrel. The melt was then extruded, and cut into granules of an average diameter of 2 to 3 mm. The material was found to be hard, and have a white color with a fine foamed structure. The water content was 12%, as water was allowed to escape when the melt left the extruder nozzle. The granulated material so obtained was then conditioned to a water content of 17%.

(b) Injection molding of the granules obtained under (a) above

The material obtained under (a) above was fed into the hopper of an injection molding machine. The material was formed into a melt within the screw barrel. The temperature there was kept at 165° C., the pressure at $75 \times 10^5$ N/m$^2$, the average residence time was 7½ minutes (approx. 5 minutes heating time, approx. 2½ minutes molten state). The melt was injected into a mold so that test pieces were produced suitable for testing their physical properties (stress/strain behaviour) on an INSTRON tensile listing apparatus. The samples were conditioned at 13.5% water content and measured at room temperature using an extension rate of 10 mm per minute.

FIG. 1 shows the stress/strain diagram for a material produced according to Example 1(b) with a residence time of 450 seconds, a screw speed of 75 rpm, a break strain of 32.5±2.0%, a break stress of 40.0±1.0 MPa and a break energy per unit area of 450.0±30.1 KJ/m$^2$.

Figure 2:
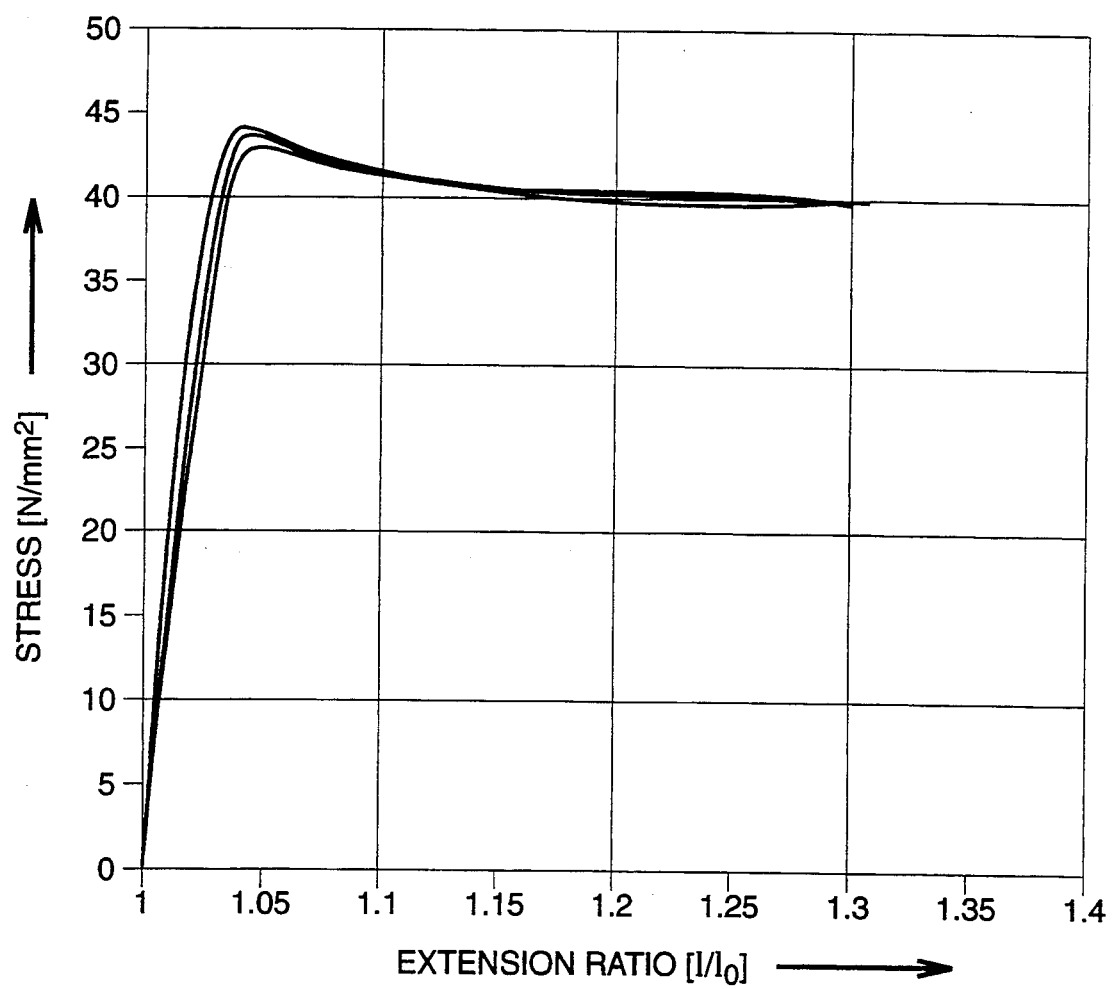
FIG. 2 illustrates the stress/strain behavior of starch processed at a residence time of 450 seconds and a screw speed of 125 rpm.

FIG. 2 shows the stress/strain diagram for a further material obtained according to Example 1(b) with a residence time of 450 seconds, a screw speed of 125 rpm, a break strain of 29.4±2.0%, a break stress of 39.3±0.2 MPa and a break energy per unit area of 401±30.6 KJ/m$^2$.

The test pieces were of standard DIN design (DIN No. 53455). Each group shows results from three samples injection molded under the same processing conditions as described above under (b) using the pre-processed (destructurized) starch as obtained under (a). It is immediately apparent that the test pieces are well reproducible in properties and the extension to break is about 30%. This is consistently and remarkably higher than the results obtained in the comparative Example 2. Other processing conditions, e.g. injection molding residence time 600 sec., screw speed 75 rpm gave analogous results.

EXAMPLE 2 (COMPARATIVE TEST TO EXAMPLE 1)

The same starting composition as described in Example 1(a) was fed into the hopper of an injection molding machine and test pieces as obtained under Example 1 (b) were directly produced in a single step process. The temperature in the screw barrel was 165° C., the pressure $75 \times 10^5$ N/m$^2$, the residence time was 12½ minutes (approx. 8 minutes for heating, approx. 4½ minutes in the molten state). The stress/strain behaviours are shown in the FIGS. 3 and 4.

Figure 3:
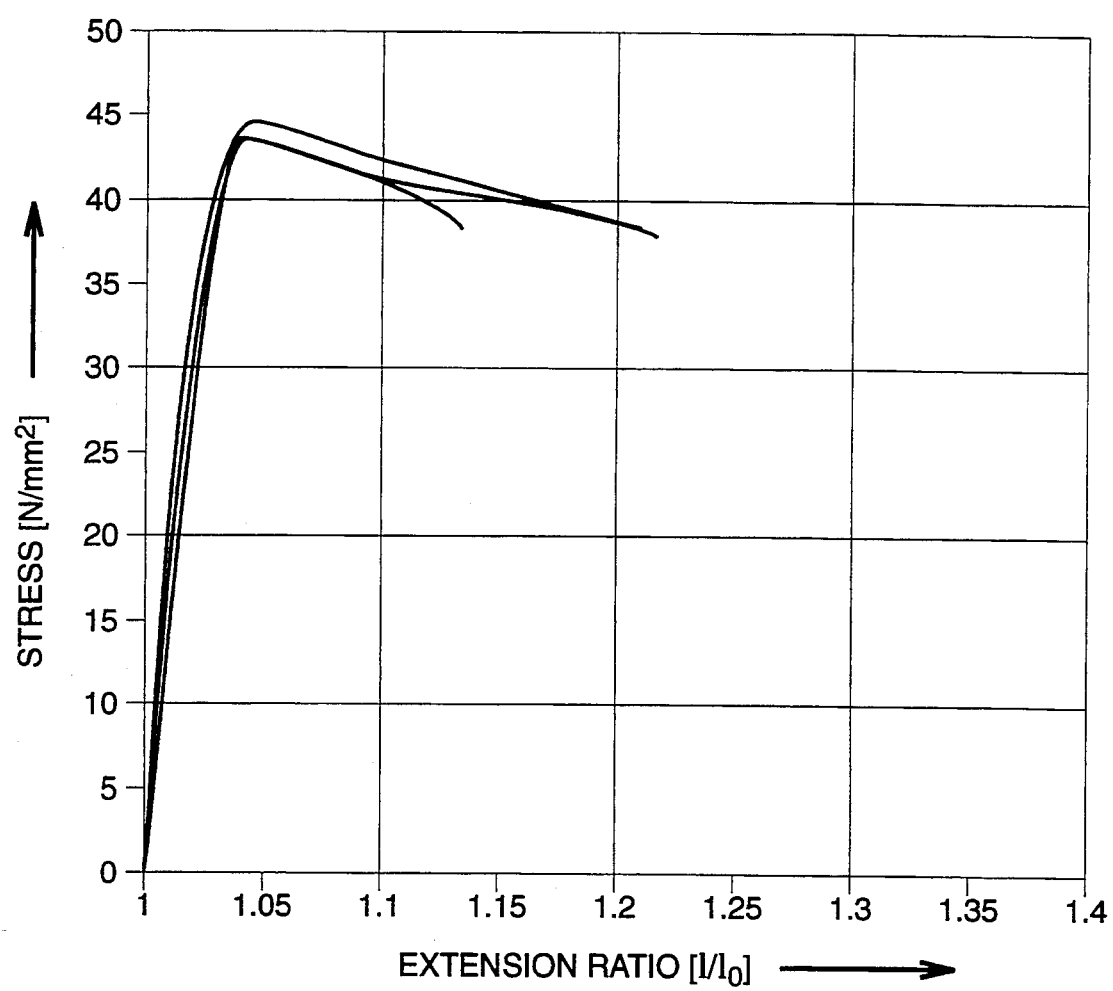
FIG. 3 illustrates the stress/strain behavior of starch processed at a residence time of 750 seconds and a screw speed of 75 rpm.

FIG. 3 shows the stress/strain diagram for a material obtained according to Example 2, with a residence time of 750 seconds, a screw speed of 75 rpm, a break strain of 18.0±4.7%, a break stress of 33.8±7.7 MPa and a break energy per unit area of 241±68 KJ/m$^2$.

Figure 4:
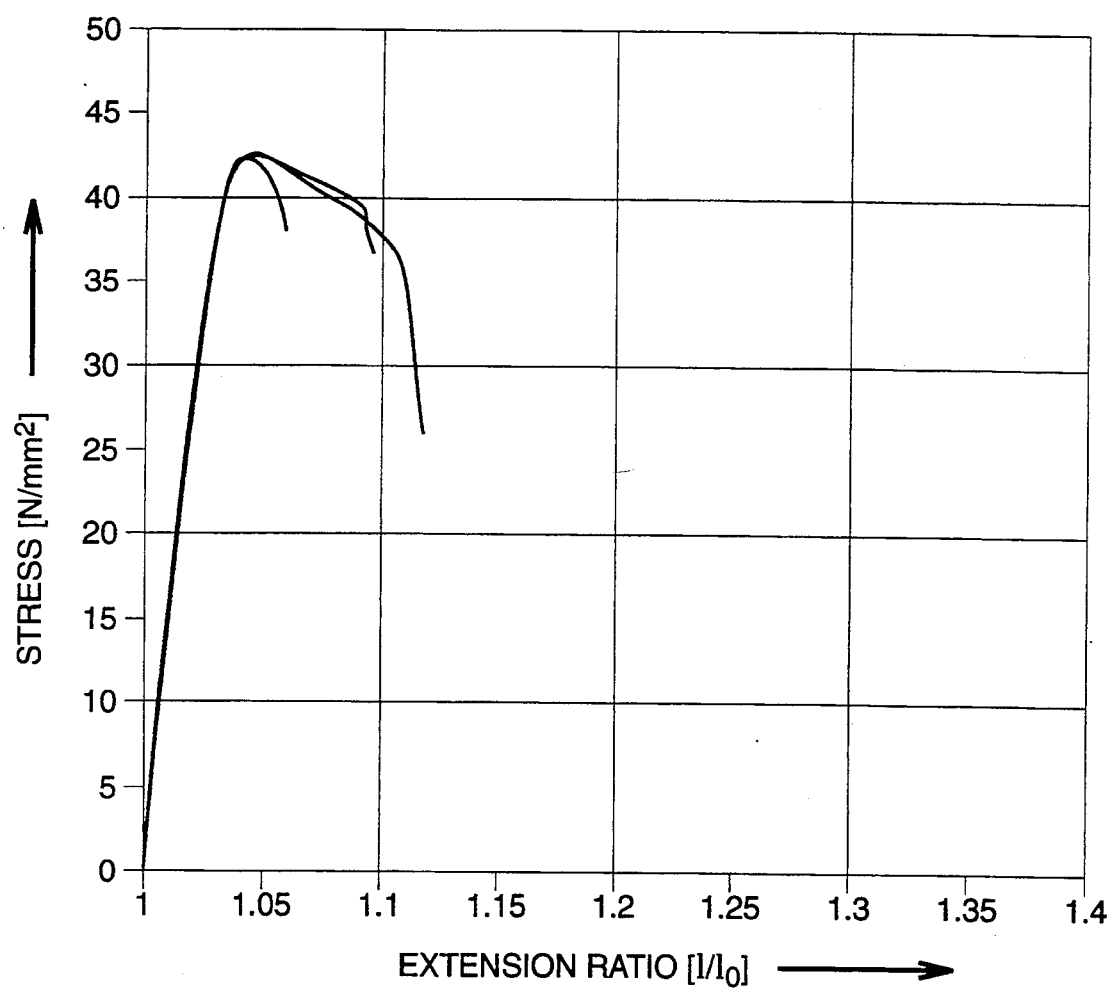
FIG. 4 illustrates the stress/strain behavior of starch processed at a residence time of 750 seconds and a screw speed of 100 rpm.

FIG. 4 shows the stress/strain diagram for a further material obtained according to Example 2, with a residence time of 750 seconds, a screw speed of 100 rpm, a break strain of 8.8±3.1%, a break stress of 33.8±7.7 MPa and a break energy per unit area of 108±44 KJ/m$^2$.

It can be seen from these results that the obtained extension values to break are relatively low, inconsistent and remarkably inferior to those obtained according to Example 1.

EXAMPLE 3

The Examples 1 and 2 were repeated but the starting composition in Example 1(a) was replaced by the following components:

| | |
|---|---|
| natural potato starch: | 80.0 parts |
| lubricant/release agent | 1.0 parts |

| | |
|---|---|
| -continued | |
| (hydrogenated fat): | |
| lecithin: | 0.7 parts |
| titanium dioxide: | 0.3 parts |
| water: | 17.0 parts |
| | 100.0 parts |

Analogous results as in Examples 1 and 2 were obtained as shown in the FIGS. 1, 2 (when processed analogously to Example 1) and FIGS. 3 and 4 (when processed analogously to Example 2).

EXAMPLE 4

Examples 1 and 2 were repeated with a composition containing polyvinylpyrrolidone, so that test pieces of following composition were obtained:

| | |
|---|---|
| potato starch: | 74.6% |
| polyvinylpyrrolidone: | 10.0% |
| hydrogenated fat: | 1.1% |
| lecithin: | 0.8% |
| water: | 13.5% |
| | 100.0% |

The stress/strain behaviour was very similar to that shown in the FIGS. 1 and 2 when processed analogously to Example 1 and to FIGS. 3 and 4 when processed analoguously to Example 2.

EXAMPLE 5

Further test pieces were molded from destructurized starch as in Example 1(b) and from native starch as in Example 2 using the same processing conditions.

Figure 5:
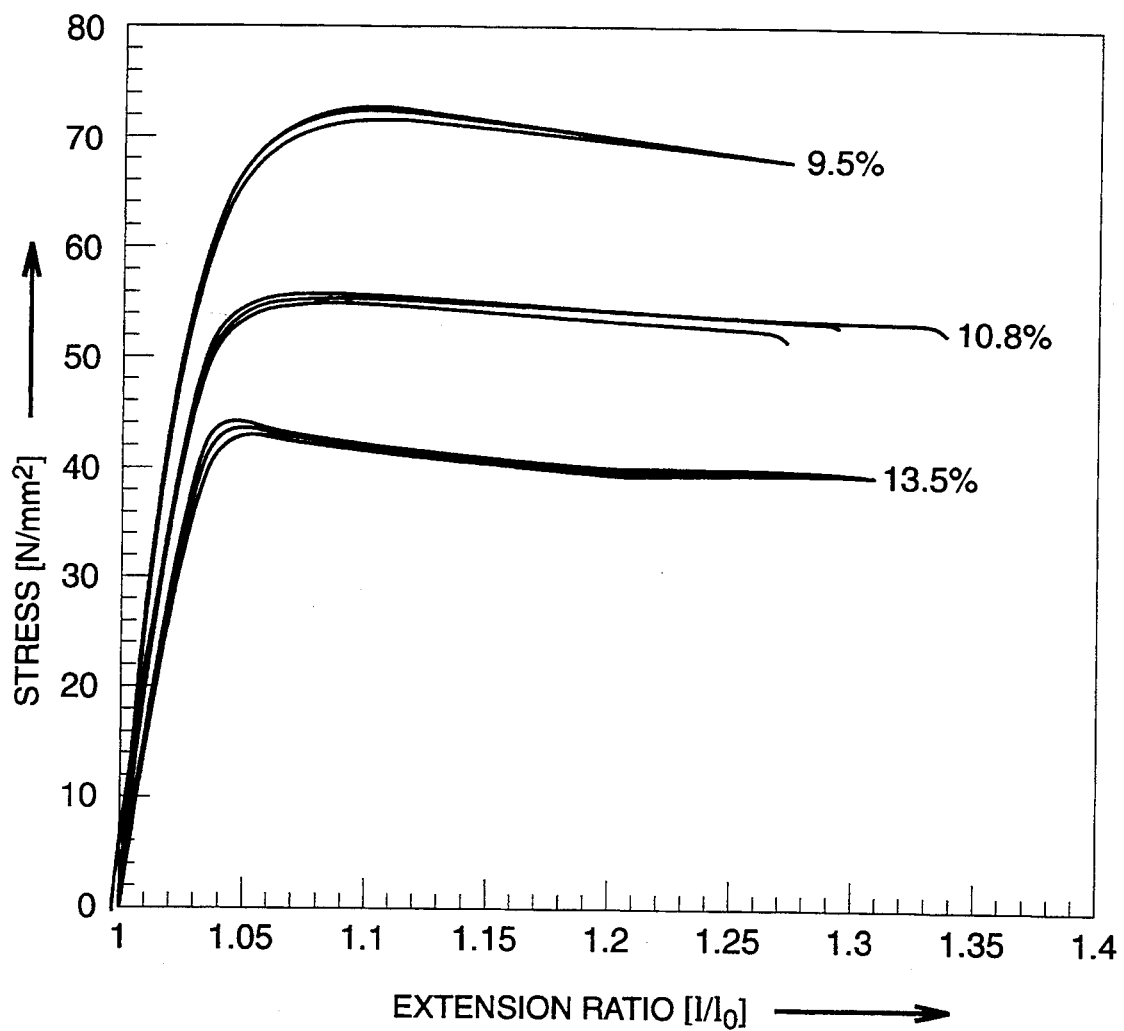
FIG. 5 illustrates the stress/strain behavior of starch processed at a residence time of 450 seconds, screw speed of 75 rpm, temperature 165° C. and pressure $75 \times 10^5$ N/m$^2$.
Figure 6:
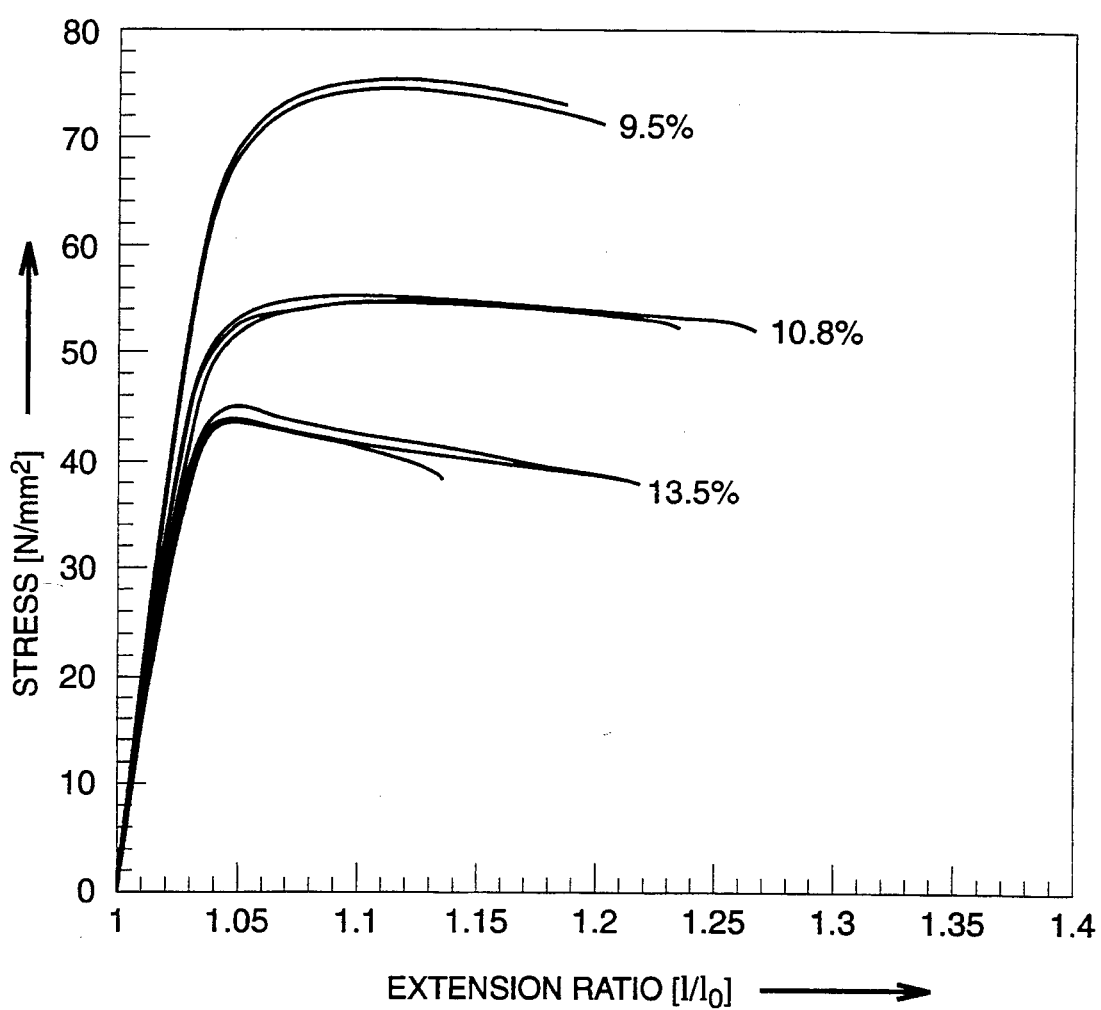
FIG. 6 illustrates the stress/strain behavior of starch processed at a residence time of 750 seconds, screw speed 75 rpm, temperature 165° C. and pressure $75 \times 10^5$ N/m$^2$.

The molded pieces were conditioned to various moisture contents, i.e., 9.5%, 10.8% and 13.5% water, and stress/strain curves determined. The results are shown in FIGS. 5 and 6. The results in FIG. 5 from pre-extruded starch are clearly superior. A homogenous material exists at all the water contents is used, with a residence time of 450 seconds, a screw speed of 75 rpm, a temperature of 165° C. and a pressure of $75 \times 10^5$ N/m². The material in FIG. 6 shows inferior properties (less extension and energy to break) and a less reproducible behaviour at all water contents, with a residence time of 750 seconds, a screw speed of 75 rpm, a temperature of 165° C. and a pressure of $75 \times 10^5$ N/m⁵. Such behaviour is consistent with a less homogenous and less coherent material.

EXAMPLE 6 (PROCESSING STABILITY)

Figure 7:
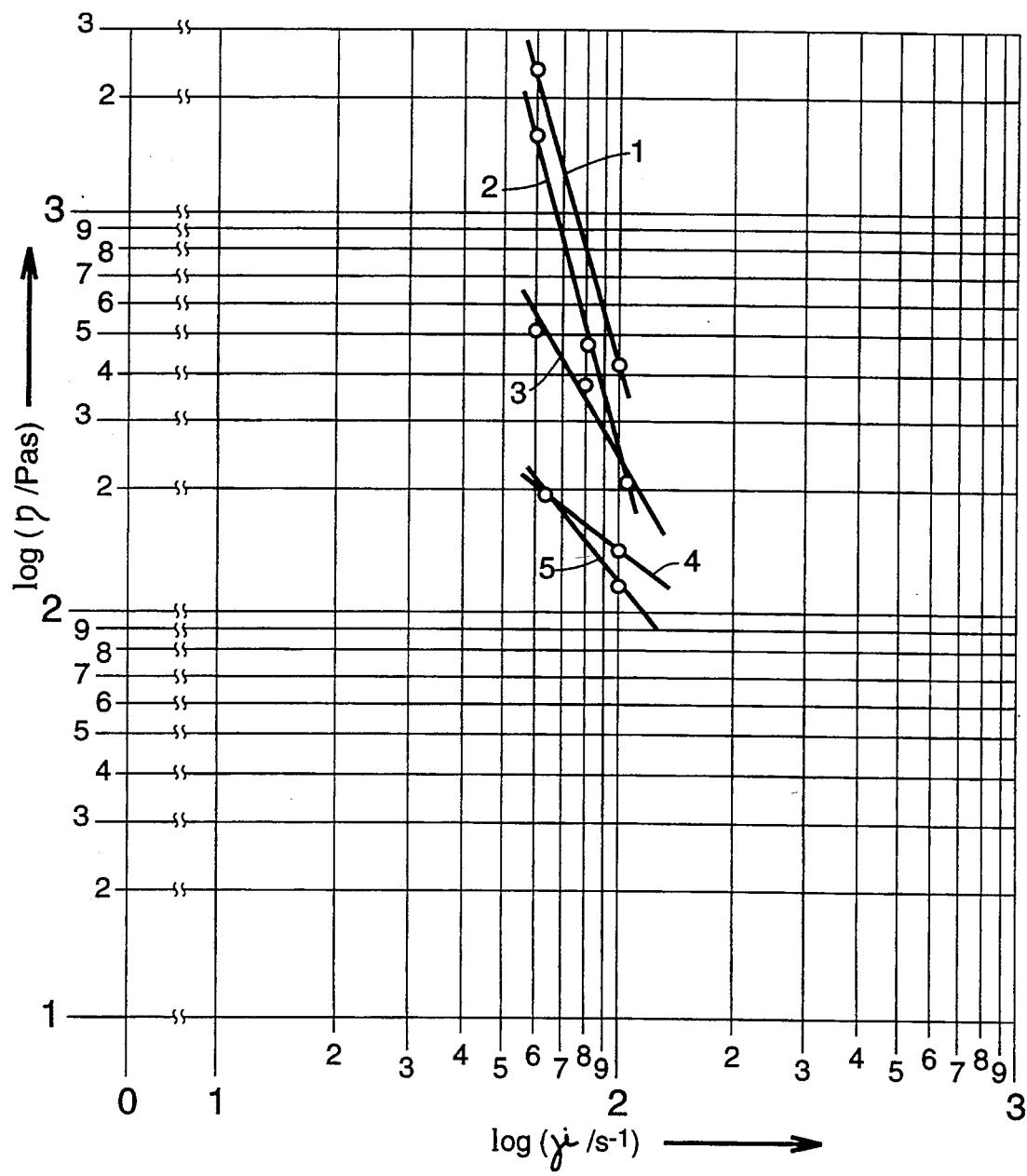
FIG. 7 illustrates melt viscosity versus shear rate for one-step and two-step processes. Lines (1), (2) and (3) represent a one-step process at residence times of 750, 600 and 450 seconds, respectively. Lines (4) and (5) represent a two-steo process at residence times of 750 and 450 seconds, respectively.

The viscosity in the molten state of the composition as described in Example 1(a) was measured as a function of the shear rate when treated (1.) as in Example 1(b) and (2.) as in Example 2. The results were obtained under well adjusted machine conditions (Netstal machine type 235/90). The melt riscosity of a function of shear rate was calculated from the measurements using standard injection-molding theory together with measurements of refill times. FIG. 7 shows the results from the two-step process according to Example 1 as well as the results from the one-step process according to Example 2. The materials processed according to Example 2 (one-step process) show higher melt viscosities with greater sensitivities to residence times and to shear rate. These higher values and sensitivities give a lower processing stability and a lower product reproducibility, which is also evident from FIGS. 3, 4 and 6.

The melt viscosity as a function of shear rate in the two-step process according to Example 1, are similar to those of conventional thermoplastics, e.g. polyethylene, which are known to be processible by injection molding to give reproducible products.

In FIG. 7 log ($\eta$/Pa s) means the logarithm to the base 10 of the value of the melt viscosity ($\eta$) in units of Pa s; log ($\gamma$/s$^{-1}$) means the logarithm to the base 10 of the value of the shear rate in units of reciprocal seconds. Lines (1), (2) and (3) represent the one-step process according to Example 2, and have residence times of 750 seconds, 600 seconds and 450 seconds, respectively. Lines (4) and (5) represent the two-step process according to Example 1, and have residence times of 750 seconds and 450 seconds, respectively.

We claim:

1. A process for forming shaped articles from starch, wherein said process comprises the steps of:
    a) heating a solid starch composition comprising starch and water, wherein the water content of said solid starch composition is about 10% to about 20% by weight with respect to that of said starch composition, said heating step taking place in a screw barrel of an injection molding machine or an extruder, at a temperature of from about 80° C. to about 200° C., and at a pressure of from about zero to about $150 \times 10^5$ N/m², for a time long enough to form a melt of destructurized starch;
    b) transferring said melt of destructurized starch to a mold or extruding said melt of destructurized starch while maintaining the water content in the range of from about 10% to about 20% by weight with respect to that of the composition; and
    c) cooling said melt of destructurized starch in said mold or outside said extruder to form a solid shaped article, wherein said solid starch composition has been obtained by heating starch and water, wherein the water content is in the range of from about 10% to about 20% by weight with respect to that of said starch, in a closed volume to a temperature within the range of about 120° C. to about 190° C. at a pressure corresponding to the vapor pressure of water at the used temperature and up to about $150 \times 10^5$ N/m², to form a melt, wherein said melt is extruded and cooled to a solidified and granulated product.

2. A process according to claim 1, wherein said starch is selected from the group consisting of chemically non-modified and physically modified starch.

3. A process according to claim 2, wherein said starch has been extracted from the group consisting of potatoes, rice, tapioca, corn, rye, oats and wheat.

4. A process according to claim 1, wherein the water content of said solid starch composition is in the range of about 12 to 19% by weight of said starch granules.

5. A process according to claim 4, wherein the water content of said solid starch composition in the range of about 14 to 18% by weight of the composition.

6. A process according to claim 1, wherein said solid starch composition is heated to a temperature of from 140° C. to 180° C.

7. A process according to claim 1, wherein the pressures applied to said solid starch composition are from zero to $100 \times 10^5$ N/m².

8. A process according to claim 7, wherein the pressures applied to said solid starch composition are from zero to $80 \times 10^5$ N/m².

9. A process according to claim 1, wherein the pressures applied to said destructurized starch melt during transfer of said melt to a mold are from $300 \times 10^5$ N/m$^2$ to $3,000 \times 10^5$ N/m$^2$.

10. A process according to claim 1, wherein the pressures applied to said destructurized starch melt during transfer of said melt to a mold are from $700 \times 10^5$ N/m$^2$ to $2,200 \times 10^5$ N/m$^2$.

11. A process according to claim 1, wherein said destructurized starch melt contains extenders, lubricants, plasticizers, inorganic fillers and/or coloring agents.

12. A process according to claim 1, wherein said destructurized starch melt contains at least one member selected from the group consisting of extenders, vegetable proteins, blood proteins, egg proteins, acrylated proteins, water-soluble polysaccharides, carrageenans, guar gum, agar-agar, gum arabic, gum ghatti, gum karaya, gum tragacanth, pectin, water-soluble derivatives of cellulose, polyacrylic acids and polyacrylic acid esters, polymethacrylic acids and polyacrylic acid esters, polyvinylacetates, polyvinylalcohols, polyvinylacetatephthalates, (PVAP), polyvinylpyrrolidone, polycrotonic acids, phtalated gelatin, gelatin succinate, cross-linked gelatin and cationically modified polymers of acrylates and/or methacrylates, in an amount of up to about 5%, based on the weight of all components.

13. A process according to claim 1, wherein said destructurized starch melt contains or is mixed with at least one member selected from the group consisting of gelatin, sunflower proteins, alginates, alkylcelluloses, hydroxyalkylcelluloses, hydroxyalkylalkylcelluloses, cellulose esters, hydroxyalkylcellulose esters, carboxyalkylcelluloses, and carboxyalkylcellulose esters, in an amount up to 50%, based on the weight of all components.

14. A process according to claim 1, wherein said destructurized starch melt contains or is mixed with at least one plasticizer selected from the group consisting of polyalkylene oxides, glycerol, glycerol monoacetate, glycerol diacetate, glycerol triacetate, propylene glycol, sorbitol, sodium diethylsulfosuccinate, triethyl citrate, and tributyl citrate, added in concentrations ranging from 0.5 to 15% based on the weight of all the components.

15. A process according to claim 1, wherein said destructurized starch melt contains or is mixed with at least one member selected from the group consisting of polyethylene glycols, polypropylene glycols, and polyethylene-propylene glycols, added in concentrations ranging from 0.5 to 15% based on the weight of all the components.

16. A process according to claim 1, wherein said destructurized starch melt contains or is mixed with at least one coloring agent selected from the group consisting of azo dyes, organic pigments, inorganic pigments, and coloring agents of natural origin, being added in concentrations ranging from 0.001 to 10%, based on the weight of all components.

17. A process according to claim 1, wherein said destructurized starch melt contains or is mixed with inorganic fillers in a concentration in the range of about 0.02 to 3% by weight, based on the weight of all components.

18. A process according to claim 11, wherein a plasticizer is present and the sum of said plasticizer and water content does not exceed 25%, based on the weight of all the components.

19. A process according to claim 1, wherein said destructurized starch melt comprises or is mixed with a material comprising animal or vegetable fats.

20. A process according to claim 19, wherein said animal or vegetable fats are in their hydrogenated form.

21. A process according to claim 1, wherein said destructurized starch melt comprises or is mixed with a material comprising fat together with mono and/or diglycerides or phosphatides, especially lecithin, whereby the total amounts used of the fats, mono-, diglycerides and/or lecithins are up to 5% by weight of the total composition.

22. A process according to claim 1, wherein said destructurized starch melt contains or is mixed with silicon dioxide or titanium dioxide in a concentration of 0.02 to 1% by weight of the total composition.

23. A process of forming a destructurized starch melt, wherein said process comprises the steps of:
heating a solid starch composition comprising starch and water, wherein the water content of said solid starch composition is about 10% to about 20% by weight with respect to that of said solid starch composition, and wherein said heating step taking place in a screw barrel of an injection molding machine or an extruder, at a temperature of from about 80° C. to about 200° C., and at a pressure of from about zero to about $150 \times 10^5$ N/m$^2$, for a time long enough to form a melt of destructurized starch; wherein said solid starch composition has been obtained by heating starch and water, wherein the water content is in the range of from about 10% to about 20% by weight with respect to that of said starch and water, in a closed volume to a temperature within the range of about 120° C. to about 190° C. at a pressure corresponding to the vapor pressure of water at the used temperature and up to about $150 \times 10^5$ N/m$^2$, to form a melt, wherein said melt is extruded and cooled to a solidified and granulated product.

* * * * *

UNITED STATES PATENT AND TRADEMARK OFFICE
CERTIFICATE OF CORRECTION

PATENT NO. : 5,405,564
DATED : April 11, 1995
INVENTOR(S) : Robert F. T. Stepto. et al It is certified that error appears in the above-indentified patent and that said Letters Patent is hereby corrected as shown below:

COLUMN 1

Line 30, "the" should be deleted; and

Line 59, "article" should read --article,--.

COLUMN 2

Line 15, "content" should read --content;--;

Line 50, "two-steo" should read --two-step--; and

Line 55, "is-interesting" should read --is interesting--.

COLUMN 3

Line 8, "conditions" should read --conditions,--;

Line 12, "transitions point" should read --transition points--;

Line 26, "vapour" should read --vapor--;

Line 52, "with" should read --more preferably within--;

Line 57, "vapour" should read --vapor--;

Line 58, "volume" should read --volume,--; and

Line 68, "2200 $10^5$ N/m$^2$" should read --2200 x $10^5$ N/m$^2$--.

UNITED STATES PATENT AND TRADEMARK OFFICE
CERTIFICATE OF CORRECTION

PATENT NO. : 5,405,564
DATED : April 11, 1995
INVENTOR(S) : Robert F. T. Stepto. et al It is certified that error appears in the above-indentified patent and that said Letters Patent is hereby corrected as shown below:

COLUMN 4:

Line 15, "tragacauth)" should read --tragacanth)--;

Line 16, "alkylcelluloses" should read --alkylcelluloses,--; and

Line 31, "phtnulated" should read --phthalated--.

COLUMN 5:

Line 44, "81,3" should read --81.3--; and

Line 54, "vapour" should read --vapor--.

COLUMN 6:

Line 11, "1(b)" should read --1(b),--; and

Line 16. "1(b)" should read --1(b),--.

COLUMN 7:

Line 27, "analogu-" should read --analog- --;

Line 29, "analoguously" should read --analogously--; and

Line 57, "riscosity" should read --viscosity--.

COLUMN 8

Line 58, "composition" should read --composition is--.

UNITED STATES PATENT AND TRADEMARK OFFICE
CERTIFICATE OF CORRECTION

PATENT NO. : 5,405,564
DATED : April 11, 1995
INVENTOR(S) : Robert F. T. Stepto, et al It is certified that error appears in the above-indentified patent and that said Letters Patent is hereby corrected as shown below:

COLUMN 9:

Line 23, "tephthalates," should read --tephthalates--; and

Line 24, "phtalated" should read --phthalated--.

COLUMN 10:

Line 32, "steps" should read --step--; an

Line 37, "taking" should read --takes--.

Signed and Sealed this

Twenty-fourth Day of October, 1995

Attest:

BRUCE LEHMAN

Attesting Officer    Commissioner of Patents and Trademarks